United States Patent [19]

Koenig et al.

[11] 4,240,964
[45] Dec. 23, 1980

[54] 2-(O-HYDROXYPHENYL)-PYRROLE AND PROCESS FOR ITS PREPARATION

[75] Inventors: Horst Koenig, Ludwigshafen; Albrecht Franke, Wachenheim; Fritz-Frieder Frickel, Ludwigshafen; Wolfgang Steglich; Norbert Engel, both of Bonn, all of Fed. Rep. of Germany

[73] Assignee: BASF Aktiengesellschaft, Fed. Rep. of Germany

[21] Appl. No.: 64,906

[22] Filed: Aug. 8, 1979

[30] Foreign Application Priority Data

Aug. 12, 1978 [DE] Fed. Rep. of Germany ....... 2835439

[51] Int. Cl.³ ............................................ C07D 207/44
[52] U.S. Cl. ...................... 260/326.5 M; 260/326.5 L
[58] Field of Search ................................. 260/326.5 M

[56] References Cited

U.S. PATENT DOCUMENTS 2,489,000  11/1949  Valentine, Jr. .............. 260/326.5 M Primary Examiner—José Tovar
Attorney, Agent, or Firm—Keil & Witherspoon

[57] ABSTRACT 2-(o-Hydroxyphenyl)-pyrrole and a process for its preparation, wherein o-benzyloxybenzoic acid allylamide is reacted with phosgene in an inert solvent, the resulting imide-chloride is cyclized in the presence of a strong sterically hindered base and the benzyl protective group is then removed by hydrogenolysis.

2-(o-Hydroxyphenyl)-pyrrole is a valuable intermediate for the synthesis of drugs. In particular, alkylaminohydroxypropyl ethers thereof can, because of their β-sympatholytic actions, be used for the treatment of coronary cardiac diseases, cardiac arrhythmias and hypertonia.

2 Claims, No Drawings

2-(O-HYDROXYPHENYL)-PYRROLE AND PROCESS FOR ITS PREPARATION

The present invention relates to 2-(o-hydroxyphenyl)-pyrrole of the formula 1

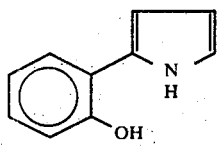

which is valuable intermediate for chemical syntheses.

2-(o-Hydroxyphenyl)-pyrrole is prepared by a process wherein o-benzyloxybenzoic acid allylamide is reacted with phosgene in an inert solvent, the resulting imide-chloride is cyclized in the presence of a strong sterically hindered base and the benzyl protective group is then removed by hydrogenolysis.

The process of preparation may be represented by the following equation

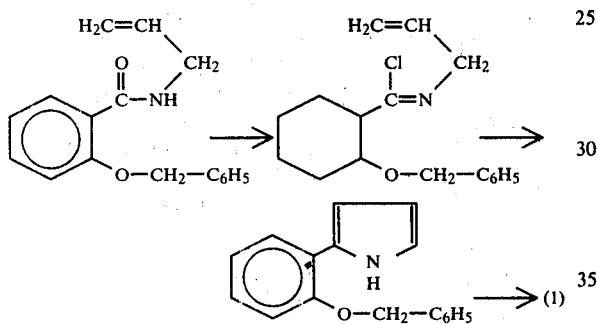

The starting compound, o-benzyloxybenzoic acid allylamide, can be obtained in the conventional manner from methyl o-benzyloxybenzoate and allylamine, or reacting 0-benzylsalicylic acid chloride with allylamine.

The reaction of o-benzyloxybenzoic acid allylamide with phosgene is effected by stirring in an inert solvent, advantageously at room temperature. Examples of suitable solvents are aromatic hydrocarbons, especially a benzene hydrocarbons, eg. benzene and toluene, aliphatic halohydrocarbons, eg. methylene chloride, chloroform or carbon tetrachloride, ethers, especially saturated cycloaliphatic ethers, eg. tetrahydrofuran or dioxane, and acetonitrile.

As a rule, phosgene solutions of 20 per cent strength by weight are used. In a preferred embodiment, a small catalytic amount of dimethylformamide is added to the reaction mixture.

The preferred solvent for the reaction with phosgene is toluene.

After the reaction, if necessary, the solvent used is distilled off, advantageously at elevated temperature under reduced pressure, and the resulting imidechloride is cyclized by means of a strong sterically hindered base.

Suitable strong sterically hindered bases are sodium alcoholates or potassium alcoholates of tert.-butanol or of 2-methylbutan-2-ol, or, for example, 1,5-diazabicyclo- 5,4,0-undec-5-ene (DBU).

The cyclization is advantageously carried out in a monofunctional or difunctional saturated aliphatic or cyclic ether, eg. tetrahydrofuran, dioxane or glycol dimethyl either, or in dimethylformamide, dimethylsulfoxide or hexamethylphosphoric acid triamide, or in a benzene hydrocarbon, eg. benzene or toluene, as the solvent, at from 0 to 150° C. Mixtures of the said solvents may also be used.

It is advantageous to carry out the cylinders in the absence of atmospheric oxygen, under an inert gas, for example under nitrogen or argon.

The preferred solvent for the cylinders reaction is tetrahydrofuran or a mixture of tetrahydrofuran and benzene or toluene, and the preferred base is potassium tert.-butylate.

The resulting o-benzyloxyphenyl-pyrrole is worked up in the conventional manner, such as by distilling off the solvent, partitioning the residue in a two-phase mixture of water and an organic solvent, for example methylene chloride or diethyl ether, and separating off the organic phase, or by chromatography over a silica gel column, using methylene chloride.

The benzyl protective group is removed in the conventional manner by hydrogenation in the presence of palladium-on-charcoal as the catalyst, the reaction being carried out in a lower alcohol. eg. methanol or ethanol, as the solvent.

The compound according to the invention, 2-(o-hydroxyphenyl) -pyrrole, is a valuable intermediate for the synthesis of pharmacologically active compounds.

For example, alkylamino-hydroxypropyl ethers may be obtained by alkylation with a epihalohydrin or an α,ω- dihalo-propan-2-ol and subsequent reaction with an amine to give the aminopropanol compound of the formula

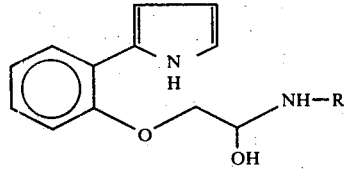

where R is alkyl of 3 to 6 carbon atoms branched at the carbon in the α-position to the nitrogen, or is alkynyl of 3 to 6 carbon atoms or is cyclopropyl; these ethers, because of their β-sympatholytic action, are particularly suitable for the treatment of coronary cardiac diseases, cardiac arrhythmias and hypertonia.

The Examples which follow illustrate the invention.

1. o-Benzyloxybenzoic acid allylamide (A) 30 g of methyl o-benzyloxybenzoate and 15 ml of allylamine are refluxed for 7 days. The residue is recrystallized from ether at -25° C.

Yield: 17.2 g, corresponding to 52% of theory; melting point 48° C.

(B) 4.9 g (20 millimoles) of 0-benzylsalicylic acid chloride in 10 ml of dioxane are introduced slowly into an ice-cooled solution of 1.7 g (30 millimoles) of allylamine and 4 g of sodium bicarbonate in 100 ml of water, and the mixture is stirred overnight. The product is filtered off, and recrystallized as under (A). Yield: 4.3 g, corresponding to 80% of theory.

2. 2-(o-Benzyloxypenyl)-pyrrole 2.7 (10 millimoles) of o-benzyloxybenzoic acid allylamide in 20 ml of a 20 per cent strength by weight solution of phosgene in tuluene are stirred, in the presence of 2 drops of dimethylformamide, at room temperature overnight. The residue which remains after distilling off the toluene under reduced pressure at 40° C. bath temperature is taken up in 30 ml of tetrahydrofuran, and the solution is filtered through a pad of glass wool and introduced, in the course of 45 minutes, into an ice-cooled solution of 4.0 g (30 millimoles) of potassium tert.-butylate in 60 ml of a 1:1 (by volume) tetrahydrofuran/benzene mixture, under argon as protective gas. 10 minutes after completion of the addition, the solvent is distilled off under reduced pressure, the residue is partitioned between methylene chloride and water, and the water is extracted twice with methylene chloride.

The combined organic phases are dried over sodium sulfate and evaporated, and the residue is chromatographed over a short silica gel column (30 ×2 cm), using carbon tetrachloride as the eluant. The oil which remains after concentrating the eluates is recrystallized from methanol. Yield: 1.4 g, corresponding to 56% of theory; melting point 72° C.

Analysis: $C_{17}H_{15}NO$ 249.3
calculated: 81.90 C 6.06 H 5.62 N
found: 81.76 C 6.00 H 5.45 N 3. 2-(o-Hydroxyphenyl)-pyrrole 150 mg of 10% strength palladium-on-charcoal catalyst are added to 1.5 g (6 millimoles) of 2-(o-benzyloxyphenyl) -pyrrole in 30 ml of methanol and hydrogenation is carried out under slightly superatmospheric pressure. The residue which remains after separating off the catalyst and evaporating the filtrate is recrystallized from toluene/petroleum ether (40°/60° C.). the yield is 0.8 g, ie. 84% of theory; melting point 100–101° C.

Analysis: $C_{10}H_9NO$ 159.19
calculated: 75.45 C 5.70 H 8.80 N
found: 75.40 C 5.70 H 8.76 N Examples of compounds of the formula 2 which may be used, where appropriate, in the form of one of their physiologically acceptable addition salts with an acid, are:
2-[2-(3-tert.-butylamino-2-hydroxypropoxy)-phenyl]-pyrrole,
2-[2-(3-isopropylamino-2-hydroxypropoxy)-phenyl]-pyrrole,
2-[2-(3-cyclopropylamino-2-hydroxypropoxy)-phenyl]-pyrrole,
2-[2-(3-sec.-butylamino-2-hydroxypropoxy)-phenyl]-pyrrole,
2-[2-(3-(3-methyl-but-l-yn-3-yl-amino)-2-hydroxypropoxy]- phenyl]-pyrrole and 2-]2-]3-(but-1-yn-3-yl-amino)-2-hydroxypropoxy]-phenyl]-pyrrole.

Regarding the use, action and determination of β-blocking agents, reference may be made, for example, to C.T. Dollery et at., Clinical Pharmacology and Therapeutics, 10(1969), No. 6, 765–799, and the literature references quoted there.

Therapeutic agents or formulations which in addition to conventional carriers and diluents contain a compound of the formula 2 or a physiologically acceptable acid addition salt thereof as the active ingredient are formulated in the conventional manner, using conventional carriers of diluents and conventional pharmacological assistants, in accordance with the desired route of administration, and so as to contain a suitable dose of the active ingredient.

For man, suitable unit doses of these compounds are from 1 to 100 mg, preferably from 3 to 50 mg.

EXAMPLE I

2-[2-(2,3 -Epoxypropoxy)-phenyl]-pyrrole 7.0 g of 2-(hydroxyphenyl)-pyrrole, 7.3 g of epibromohydrin and 11.4 g of dry potassium carbonate in 50 ml of acetone are refluxed for 7 hours. After the mixture has cooled, it is filtered and the filter residue is washed with acetone. The combined filtrates and freed from solvent by distilling off the latter. The residue is twice chromatographed on silica gel, using methylene chloride as the eluant, and thereby gives 4.6 g (48% of theory) of 2-[2- (2,3-epoxypropoxy)-phenyl]-pyrrole as a colorless oil.

$^1$H-HMR spectrum ($CDCl_3$, with TMS as an internal standard): $\delta = 2.65$ (m, 2H); 3.25-3.6 (m, 1H); 4.23 (m, 2H); 6.28 (m, 1H); 6.68 (m, 5H); 7.59 (m, 1H); 10.0 (broad, 1H).

EXAMPLE II 1.5 g of 2-[2-(2,3-epoxypropoxy)-phenyl]-pyrrole and 1 ml of tert.-butylamine in 5 ml of ethanol are left to stand overnight and the solvent and excess amine are then distilled off. The waxy residue is dissolved in a small amount of ethanol and a solution of fumaric acid in ether is added dropwise. The 2-[2-(3-tert.-butylamino-2- hydroxypropoxy)-phenyl]-pyrrole fumarate which precipitates is filtered off, washed dry ether and then dried.

Yield: 1.8 g (74% of theory); melting point 197°–198° C.

$C_{19}H_{26}O_4N_2$ (346)
calculated: 65.8 C; 7.6 H; 8.1 N.
found: 65.3 C; 7.5 H; 7.9 N.

EXAMPLE III 1.5 g of 2-[2-(2,3-epoxypropoxy)-phenyl]-pyrrole and 3 ml of isopropylamine are reacted by the method described in Example 1. After recrystallizing the product from a 1:1 methanol-ethanol mixture, 0.7 g (30% of theory) of 2-[2-(3-isopropylamino-2-hydroxypropoxy)-phenyl]-pyrrole fumarate hemihydrate, of melting point 176°–177° C., are obtained.

$C_{18}H_{24}O_4N_2 \cdot 1/2\ H_2$ (341)
calculated: 63.3 C; 7.3 H; 8.21 N.
found: 63.4 C; 7.2 H; 8.1 N.

The pharmacodynamic properties were examined by the following methods.

The β-sympatholytic action was tested on rats, in comparison with the known β-sympatholytic agent propranolol (1-isopropylamino)-1-naphthyloxy-2-propanol.HCl).

1. $\beta_1$-sympatholytic action

Isoproterenol (0.1 ug/kg. given intravenously) in pithed rats (Sprague-Dawley, Mus rattus; weight 230–280 g) causes increases in pulse rate of, on average, 45% . β-Sympatholytic agents inhibit such tachycardia. Isoproternol was administered before, and 5 minutes after, the intravenous administration of the test substances. Linear relationships are found between the logarithms of the admininstered doses (mg/kg) of the test substances and the inhibition of the isoproterenol-induced tachycardia (%). From these relationships, the ED 50% is determined as the dose which inhibits the isoproterenol -induced tachycardia by 50% .

2. Acute toxicity

The acute toxicity was determined on groups of 10 female NMRI mice, weight 19-27 g, with intraperitoneal administration. The LD 50 was calculated (by Probit analysis) as the dose after which 50% of the animals died within 24 hours. Table 1 shows that the pharmacotherapeutically important $\beta_1$-sympatholytic activity of the compounds according to the invention is 5.6 times greater (Example II) or 3.2 times greater (Example III) than that of the comparative substance propranolol. The therapeutic range, expressed as the quotient of the 50% lethal dose (LD 50) and the $\beta_1$-blocking dose (ED 50%) is 4 times greater (Example III) or 7 times greater (Example II) than that of propranolol.

TABLE 1

| Compound | $\beta_1$-sympatholytic action[1] ED 50%[2] | R.A.[3] | Acute toxicity LD 50[4] | Therapeutic range[5] absolute | relative[6] |
|---|---|---|---|---|---|
| Propranolol | 0.0127 | 1.00 | 108 | 111 | 1.00 |
| Example II | 0.00227 | 5.59 | 165 | 767 | 6.91 |
| Example III | 0.004 | 3.18 | 97.2 | 452 | 4.07 |

[1] Inhibition of isoproterenol-induced tachycardia in pithed rats. Intravenous administration
[2] Dose which inhibits the isoproterenol-induced tachycardia by 50%
[3] Relative activity. Propranolol = 1.00
[4] $\frac{LD\ 50}{ED\ 50\%}$
[6] Propranolol = 1.00

We claim:
1. 2-(o-Hydroxyphenyl)-pyrrole.
2. A process for the preparation of 2-(o-hydroxyphenyl)-pyrrole, wherein o-benzyloxybenzoic acid allylamide is reacted with phosgene in an inert solvent, the resulting imidechloride is cyclized in the presence of a strong sterically hindered base and the benzyl protective group is then removed by hydrogenolysis.

* * * * *